(12) United States Patent
Kojima et al.

(10) Patent No.: US 10,219,763 B2
(45) Date of Patent: Mar. 5, 2019

(54) PHOTON COUNTING CT DEVICE AND ESTIMATED EXPOSURE LEVEL COMPUTATION METHOD

(71) Applicant: Hitachi, Ltd., Tokyo (JP)

(72) Inventors: Shinichi Kojima, Tokyo (JP); Keisuke Yamakawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 177 days.

(21) Appl. No.: 15/504,827

(22) PCT Filed: Aug. 6, 2015

(86) PCT No.: PCT/JP2015/072422
§ 371 (c)(1),
(2) Date: Feb. 17, 2017

(87) PCT Pub. No.: WO2016/039054
PCT Pub. Date: Mar. 17, 2016

(65) Prior Publication Data
US 2018/0220979 A1    Aug. 9, 2018

(30) Foreign Application Priority Data
Sep. 11, 2014   (JP) .................. 2014-185034

(51) Int. Cl.
*A61B 6/00*   (2006.01)
*A61B 6/03*   (2006.01)

(52) U.S. Cl.
CPC ............ *A61B 6/4241* (2013.01); *A61B 6/032* (2013.01); *A61B 6/542* (2013.01); *A61B 6/463* (2013.01)

(58) Field of Classification Search
CPC ................................ A61B 6/542; A61B 6/032
See application file for complete search history.

(56) References Cited

U.S. PATENT DOCUMENTS 7,924,969 B2   4/2011   Yamakawa et al.
9,295,437 B2   3/2016   Saito
(Continued)

FOREIGN PATENT DOCUMENTS

JP   2009-017984 A   1/2009
JP   2010-167165 A   8/2010
(Continued)

OTHER PUBLICATIONS

International Preliminary Report on Patentability received in corresponding International Application No. PCT/JP2015/072422 dated Mar. 23, 2017.
(Continued)

*Primary Examiner* — Dani Fox
(74) *Attorney, Agent, or Firm* — Mattingly & Malur, PC

(57) ABSTRACT

Provided is a photon counting CT device for estimating an exposure dose to a subject, precisely in a simple configuration, irrespective of a spectrum shape of X-rays being applied. An exposure dose derived from the X-rays with predetermined intensity is obtained in every energy range provided in advance, and held as exposure per band data. When an imaging condition is provided, X-rays are applied in accordance with the imaging condition thus provided, and a photon count (intensity) of the incident X-rays as to each energy range is obtained, in the shape of spectrum of the X-rays applied to a detector without placing the subject. The intensity of the incident X-rays is multiplied by the exposure per band, and the results as to all the energy ranges are added up. Accordingly, the exposure dose caused by the X-rays being applied in accordance with the provided imaging condition is estimated.

10 Claims, 10 Drawing Sheets

(56) References Cited

U.S. PATENT DOCUMENTS

| | | | |
|---|---|---|---|
| 2010/0226474 A1 | 9/2010 | Yamakawa et al. | |
| 2014/0254747 A1 | 9/2014 | Saito | |
| 2015/0282778 A1 | 10/2015 | Kato et al. | |
| 2016/0022243 A1* | 1/2016 | Nakai | A61B 6/032 378/5 |

FOREIGN PATENT DOCUMENTS

| | | | |
|---|---|---|---|
| JP | 2014-069039 A | 4/2014 | |
| JP | 2014-140707 A | 8/2014 | |

OTHER PUBLICATIONS

International Search Report of PCT/JP2015/072422 dated Oct. 27, 2015.

* cited by examiner

Fig.2
(a)
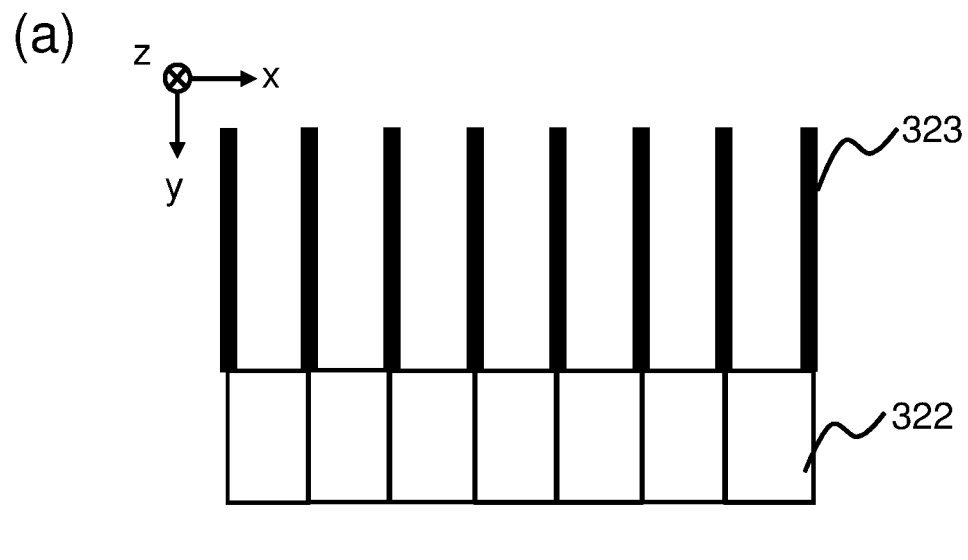
(b)
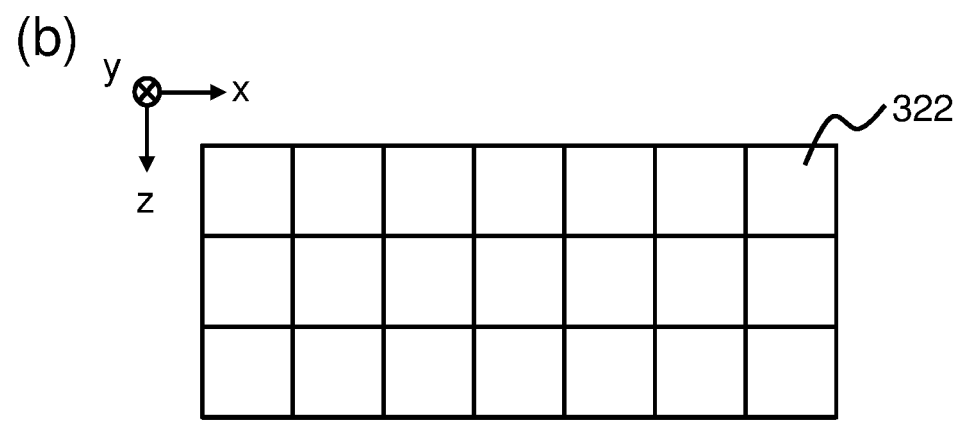

Fig.6
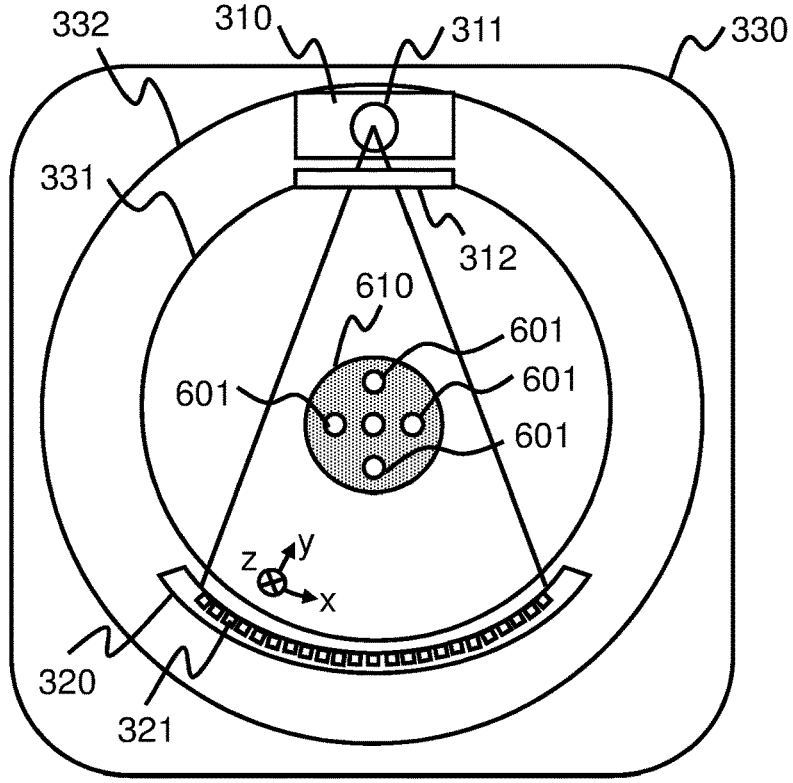
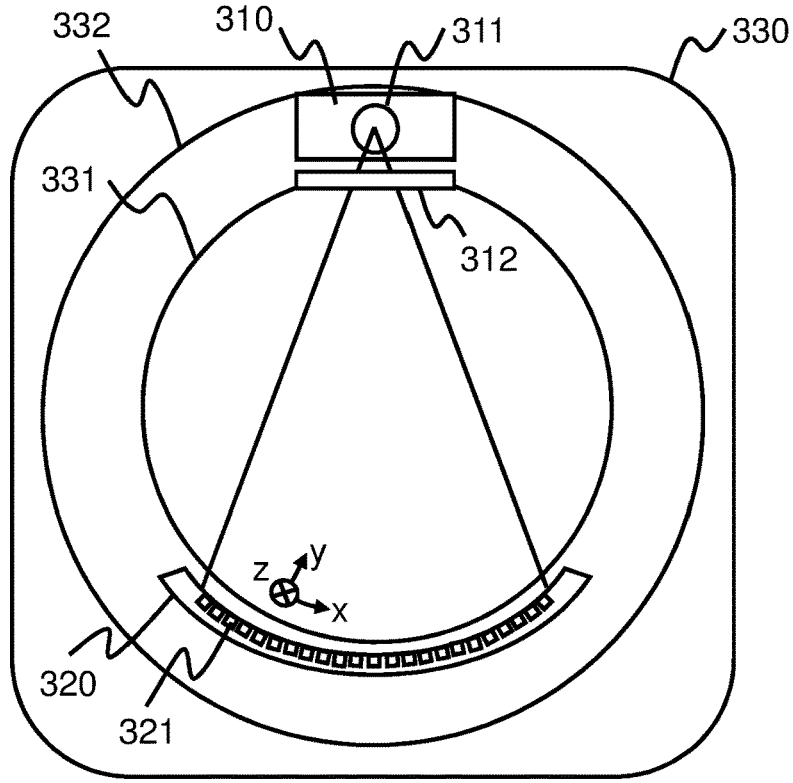

PHOTON COUNTING CT DEVICE AND ESTIMATED EXPOSURE LEVEL COMPUTATION METHOD

TECHNICAL FIELD

The present invention relates to an X-ray CT (Computed Tomography) device provided with a photon counting mode (hereinafter, referred to as a "PCCT device"). More particularly, it relates to a technique to control an exposure dose to a subject in the PCCT device.

BACKGROUND ART

An X-ray CT device acquires X-ray transmission data of a subject, along with rotating a pair of an X-ray source and an X-ray detector opposed to each other, placing the subject therebetween, and performs calculations to reconstruct a tomographic image (CT image) therefrom. Such X-ray CT device may serve as an industrial and security-use survey instrument, a medical diagnostic imaging device, and the like.

A PCCT device equipped with a photon counting mode is one of the medical X-ray CT devices. In the PCCT device, a photon counting type detector counts photons of X-rays (X-ray photons) that have passed through a subject, with respect to each detector element. This configuration allows, for example, acquisition of a spectrum that enables estimation of elements constituting internal tissue of the subject, through which X-rays have passed. Accordingly, it is possible to obtain an X-ray CT image on which element-level differences are depicted in detail.

The PCCT device categorizes individual X-ray photons being counted, according to energy values, and thus X-ray intensity can be obtained on the energy value basis. By utilizing this feature, the PCCT device may extract X-rays only within a specific energy range, for reconstructing an image to be used in diagnosis. In this case, the X-rays falling outside the energy range are attenuated to a minimum, thereby reducing an exposure dose to a patient being the subject.

A method of attenuating the X-rays outside the energy range includes, for example, a technique of inserting between the X-ray source and the subject, a thickness-variable X-ray attenuating body (hereinafter, referred to as "X-ray filter") (see Patent Document 1, for instance). The method of the Patent Document 1 allows reduction of the X-rays falling in an unnecessary energy range, by the use of the X-ray filter.

PRIOR ART DOCUMENT

Patent Document

Patent Document 1

Japanese Unexamined Patent Application Publication No. 2014-69039

DISCLOSURE OF THE INVENTION

Problems to be Solved by the Invention

It is important to precisely calculate the exposure dose, in order to reduce the exposure. In general, when tube voltage is constant, the exposure dose is calculated on the basis of current value variations. However, if filters in various forms and thicknesses are used as described in the Patent Document 1, a distribution (spectrum) of the emitted X-ray energy values may vary depending on the filter (including a bowtie filter), resulting in variations of the exposure dose. Therefore, only the variation of the current value is not sufficient for obtaining an accurate exposure dose.

The present invention has been made in view of the situation above, and it is directed to a PCCT device that precisely estimates a radiation exposure dose to a subject in a simple configuration, irrespective of the spectrum shape of emitted X-rays.

Means for Solving the Problems

An exposure dose caused by X-rays having predetermined intensity is obtained every predetermined energy range, and it is held as exposure per band data. After an imaging condition is provided, photon counts (intensity) of incident X-rays are obtained every energy range, in the form of a spectrum of the X-rays which are emitted in accordance with the provided imaging condition and incident on a detector in the state where no subject is placed. Intensity of the incident X-rays is multiplied by the exposure per band data, in every energy range, and calculation results for all the energy ranges are added up. This configuration allows estimation of an exposure dose according to the applied X-rays that are emitted in accordance with the provided imaging condition.

Advantage of the Invention

According to the present invention, the PCCT device is allowed to precisely estimate the radiation exposure dose to the subject in a simple configuration, irrespective of a spectrum shape of the emitted X-rays.

BRIEF DESCRIPTION OF THE DRAWINGS

FIG. 2(a) and FIG. 2(b) illustrate an X-ray detector according to an embodiment of the present invention;

FIG. 6(a) illustrates a method of generating the exposure per band database according to an embodiment of the present invention, and FIG. 6(b) illustrates a method of spectrum acquisition by a spectrum acquisition part according to an embodiment of the present invention;

BEST MODE FOR CARRYING OUT THE INVENTION

Figure 1:
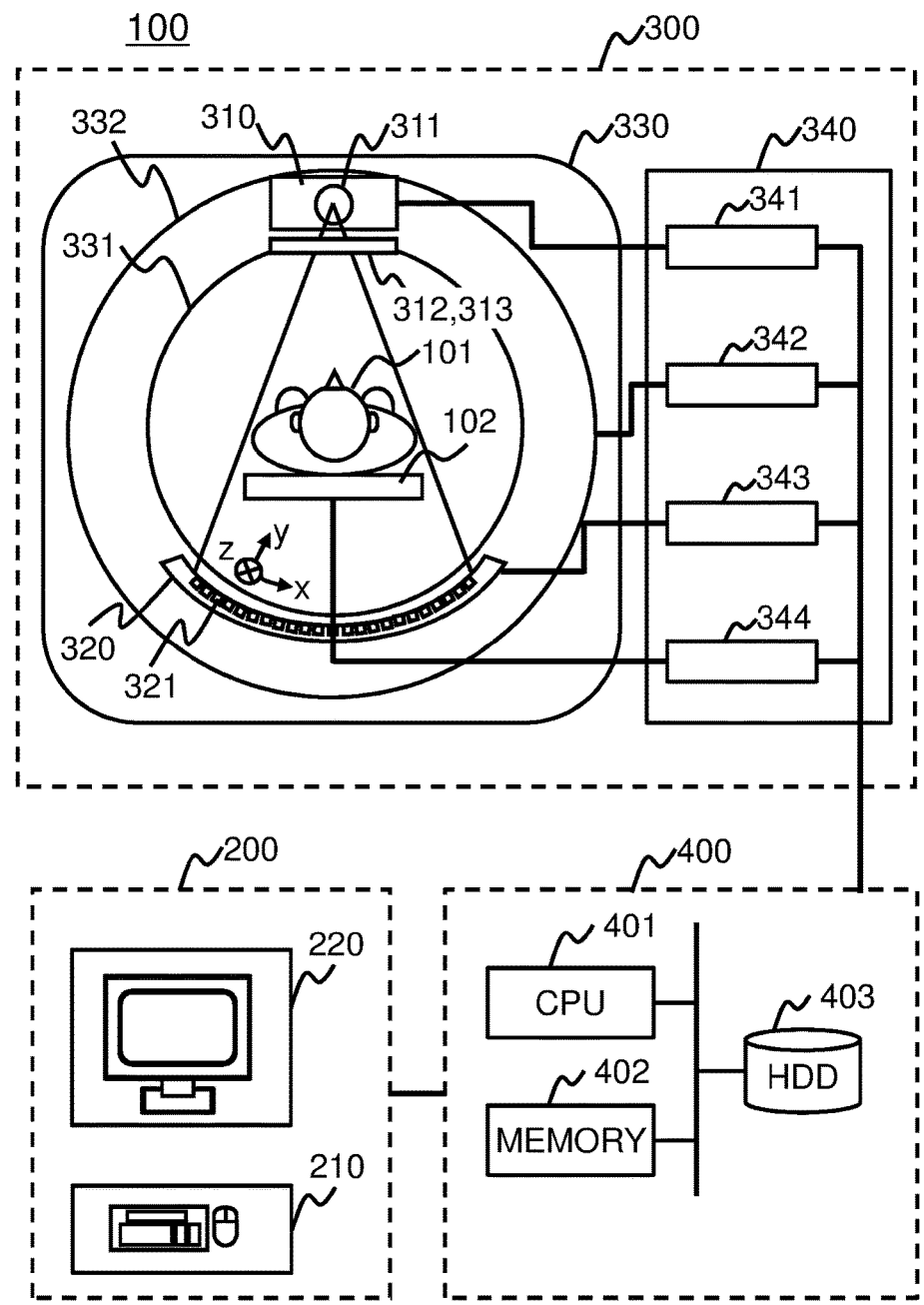
FIG. 1 is a block diagram showing a photon counting CT device according to an embodiment of the present invention.

One embodiment of the present invention will now be described. Hereinafter, in all the figures illustrating the embodiment of the present invention, elements with an identical function are labeled with the same reference numeral, and they will not be redundantly explained.

[Schematic Configuration of X-Ray CT Device]

In the present embodiment, there is used as an X-ray CT device, a photon counting CT device (PCCT device) having a detector of photon counting method, instead of a detector of conventional integral type (current mode measuring method). In the PCCT device, photons derived from X-rays (X-ray photons) that have passed through a subject are counted by the detector.

Individual X-ray photons have different energy amounts. The PCCT device counts those X-ray photons, after categorizing them into predetermined energy bands. Accordingly, the number of X-ray photons i.e., X-ray intensity in every energy band, can be obtained.

A configuration of the PCCT device 100 according to the present embodiment, provided with such features above, will be described. FIG. 1 is a schematic block diagram of the PCCT device 100 according to the present embodiment. As illustrated, the PCCT device 100 of the present embodiment is provided with a UI part 200, a measurement part 300, and an operation part 400.

The UI part 200 accepts an input from a user, and presents to the user, a processing result from the operation part 400. Therefore, the UI part 200 is provided with an input unit 210 such as a keyboard and a mouse, and an output unit 220 such as a monitor and a printer. The monitor is made up of an LCD, a CRT (Cathode Ray Tube), or the like. The monitor may be provided with a touch panel function, so as to serve as the input unit 210 as well.

[Measurement Part]

The measurement part 300 irradiates a subject 101 with X-rays according to the control by the operation part 400, and measures X-ray photons that have passed through the subject 101. The measurement part 300 is provided with an X-ray emitter 310, an X-ray detection part 320, a gantry 330, a controller 340, and a table 102 placing the subject 101 thereon.

[Gantry]

In the middle of the gantry 330, there is provided a circular opening 331 for arranging the subject 101 and the table 102 that places the subject 101 thereon. Inside the gantry 330, there are arranged a rotating panel 332 equipped with an X-ray tube 311 and an X-ray detector 321 as described below, and a drive mechanism for turning the rotating panel 332.

It should be noted that in the present specification, a circumferential direction of the opening 331 is represented as x-direction, a radial direction is represented as y-direction, and a direction orthogonal to those two directions is represented as z-direction. In general, the z-direction indicates a body axis direction of the subject 101.

[X-Ray Emitter]

The X-ray emitter 310 generates X-rays and irradiates the subject 101 with the X-rays thus generated. The X-ray emitter 310 is provided with an X-ray tube 311, an X-ray filter 312, and a bowtie filter 313.

The X-ray tube 311 irradiates the subject 101 with an X-ray beam, according to high voltage that is supplied under the control of an emission controller 341 described below. The X-ray beam being emitted spreads at a fan angle and a cone angle. The subject 101 is irradiated with the X-ray beam, along with rotation of the rotating panel 332 of the gantry 330, described in the following.

The X-ray filter 312 adjusts an X-ray dose of the X-rays emitted from the X-ray tube 311. In other words, the X-ray filter varies a spectrum of the X-rays. The X-ray filter 312 of the present embodiment attenuates the X-rays emitted from the X-ray tube 311, so that the X-rays emitted from the X-ray tube 311 toward the subject 101 form a predetermined energy distribution. The X-ray filter 312 is used to optimize an exposure dose to a patient being the subject 101. Therefore, the filter is designed in such a manner that a dose in a necessary energy band is intensified.

The bowtie filter 313 controls the exposure dose in a surrounding area. Considering that a human body being the subject 101 has an elliptical cross section, this filter is used to increase the dose around the center and reduce the dose in the periphery, thereby optimizing the exposure dose.

[X-Ray Detection Part]

The X-ray detection part 320 outputs a signal every time an X-ray photon is incident, the signal allowing measurement of an energy value of the X-ray photon. The X-ray detection part 320 is provided with an X-ray detector 321.

FIG. 2(a) shows an example of a portion of the X-ray detector 321. The X-ray detector 321 of the present embodiment is provided with plural detector elements 322 and a collimator 323 for restricting an angle of incidence toward the X-ray detector 321.

As shown in FIG. 2(a), there is a repetition of the same structure in the x-direction. As shown in FIG. 2(b), the X-ray detector 321 may have a configuration including a large number of detector elements 322 at approximately equal distances from an X-ray generation point of the X-ray tube 311, both in the x-direction and in the z-direction.

For ease of production, a plurality of planar detectors (detector modules) are created, and those detectors may be arranged in such a manner that the planes form an arc-like shape at the central part, so as to implement the X-ray detector 321.

Each of the detector elements 322 outputs an electrical signal (analogue signal) of one pulse, every time the X-ray photon enters. Then, this outputted signal is inputted in the operation part 400 described in the following.

By way of example, CdTe (cadmium telluride)-system semiconductor element may be used as the detector element 322, for directly converting the incident X-ray photons to the electrical signals. It should be noted that a scintillator that emits fluorescence upon receiving an X-ray and a photo diode that converts the fluorescence to electricity may be used as the detector element 322.

The number of the detector elements 322 (the number of channels) in the X-ray detector 321 may be 1,000, for instance. The size of each detector element in the x-direction may be 1 mm, for instance.

By way of example, a distance between an X-ray originating point of the X-ray tube 311 and an X-ray incident plane of the X-ray detector 321 may be 1,000 mm. A diameter of the opening 331 of the gantry 330 may be 700 mm.

A time required for turning the rotating panel 332 depends on a parameter inputted in the UI part 200 by a user. In the present embodiment, the time required for rotation is set to be 1.0 second per turn, for instance. The number of imaging by the measurement part 300 may be 900 times in one revolution, and every time the rotating panel 332 turns by 0.4 degrees, an image is taken one time.

The specifications above are not restricted to those values, but they may be changed variously depending on the configuration of the PCCT device 100.

[Controller]

The controller 340 is provided with the emission controller 341 configured to control X-ray emission from the X-ray tube 311, a gantry controller 342 configured to control a rotary drive of the rotating panel 332, a detection controller 343 configured to control X-ray detection by the X-ray detector 321, and a table controller 344 configured to control a drive of the table 102. Those elements are operated under the control of a measurement controller 420 in the operation part 400 described in the following.

[Operation Part]

Figure 3:
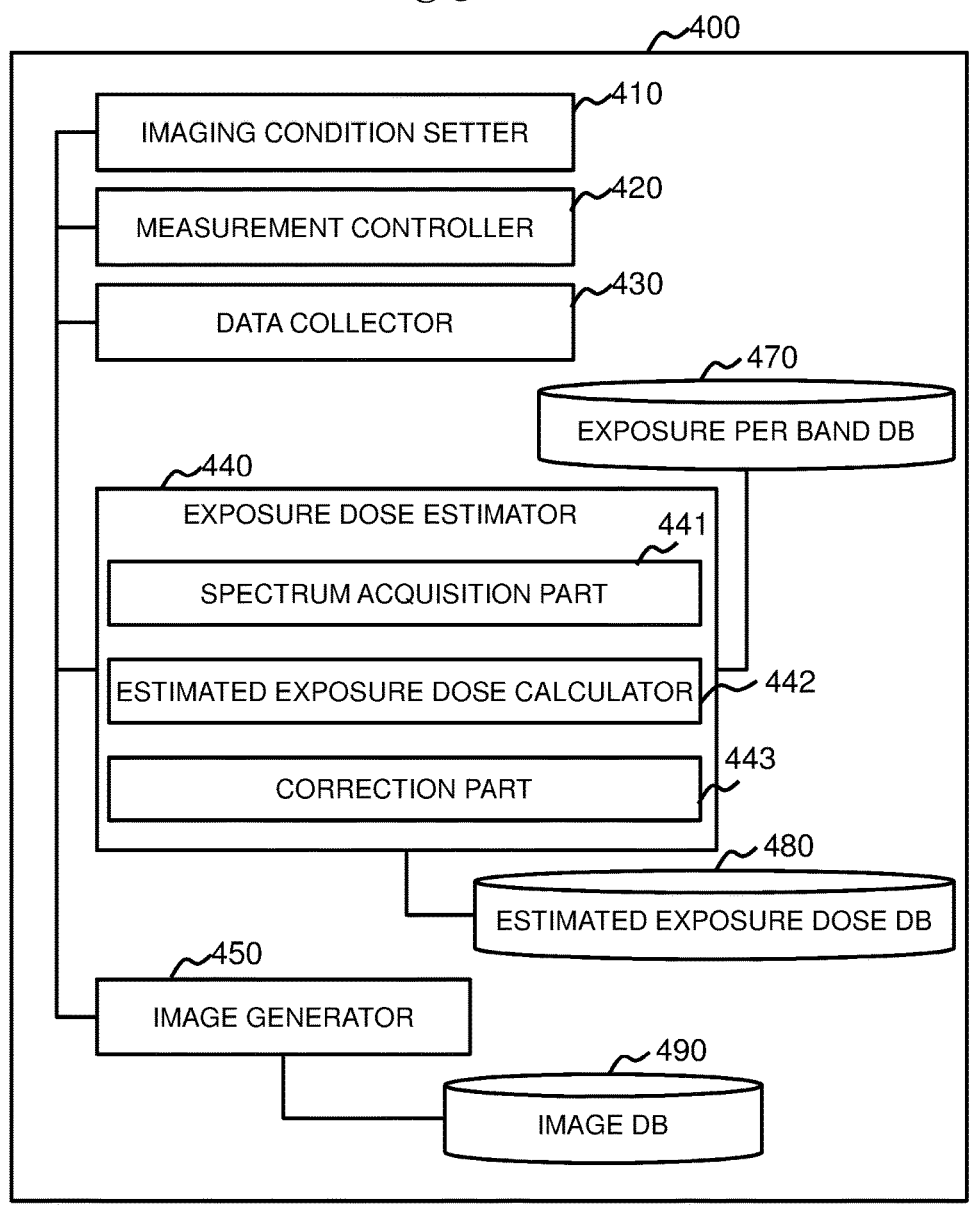
FIG. 3 is a functional block diagram of an operation part according to an embodiment of the present invention.

The operation part 400 controls the entire operation of the PCCT device 100, and performs imaging by processing data acquired by the measurement part 300. As shown in FIG. 3, the operation part 400 of the present embodiment incorporates an imaging condition setter 410, a measurement controller 420, a data collector 430, an exposure dose estimator 440, an image generator 450, and an exposure per band database (DB) 470.

The operation part 400 is provided with a CPU (Central Processing Unit) 401, a memory 402, and a HDD (Hard disk drive) unit 403. By way of example, the CPU 401 loads programs held in advance in the HDD unit 403 into the memory 402, and executes the programs, thereby implementing each of the functions above.

All or a part of the functions of the operation part 400 may be implemented, for example, by an integrated circuit such as ASIC (Application Specific Integrated Circuit), and FPGA (Field Programmable Gate Array).

In addition, the HDD unit 403 may store data, including data used for processing, data generated during processing, and data obtained as a result of the processing. The processing result may also be outputted to the output unit 220 of the UI part 200. The exposure per band DB 470 may be constructed in the HDD unit 403, for instance.

[Imaging Condition Setter]

The imaging condition setter 410 accepts an imaging condition from the user, and configures settings thereof. By way of example, the imaging condition setter 410 displays a reception screen on the monitor for entering the imaging condition, and the imaging condition is accepted via the reception screen. The user manipulates a mouse, a keyboard, or a touch panel, for example, thereby entering the imaging condition via the reception screen.

The imaging conditions being provided may include, for example, tube current and tube voltage of the X-ray tube 311, an imaging area of the subject 101, a form of the X-ray filter 312, a form of the bowtie filter 313, a resolution, and so on.

It should be noted that the imaging conditions are not necessarily entered by the user each time. By way of example, typical imaging conditions are stored in advance, and any of the conditions may be read out and used.

[Measurement Controller]

The measurement controller 420 controls the controller 340 according to the imaging condition set by the user, and executes measurement.

Specifically, the measurement controller 420 instructs the table controller 343, to move the table 102 in a direction vertical to the rotating panel 332, and to stop moving at the point when an imaging position of the rotating panel 332 coincides with the imaging position being designated. Accordingly, placement of the subject 101 is completed.

The measurement controller 420 activates a drive motor for the gantry controller 342 at the same timing as the instruction to the table controller 343, and instructs to start turning of the rotating panel 332.

When turning of the rotating panel 332 becomes constant speed and placement of the subject 101 is completed, the measurement controller 420 gives an instruction to the emission controller 341 about the X-ray emission timing of the X-ray tube 311, and also gives an instruction to the detection controller 344, about the imaging timing of the X-ray detector 321. Accordingly, the measurement controller 420 starts emission of X-rays and detection of X-ray photons, that is, starts the measurement.

The measurement controller 420 performs measurement of the entire imaging range, by repeating such instructions as described above.

It is also possible to perform control for imaging along with moving the table 102, like a publicly known helical scan.

[Data Collector]

The data collector 430 counts photons derived from the X-rays detected by the X-ray detector 321 (X-ray photons) in every energy range according to predetermined first energy-range segments, and obtains count information as to each of the energy ranges. The data collector 430 of the present embodiment is provided with a data acquisition system (hereinafter, referred to as "DAS"), and the DAS counts the X-ray photons detected by the measurement part 300.

The DAS acquires an energy value as to each X-ray photon, one by one, detected by the X-ray detector 321, and adds the energy value to a counting result in an energy bin (Bin) provided for each energy range, depending on the energy value. The energy bin is a storage area configured for each energy range according to the first energy-range segments.

The first energy-range segments are obtained by partitioning the energy range from 0 keV to the maximum energy of the X-ray tube 311, by a predetermined energy width $\Delta B$. The energy width $\Delta B$ may be 20 keV, for instance. By way of example, when the maximum energy is assumed as 140 keV, the entire energy range 0 keV to 140 keV is partitioned into seven energy-range segments; B1 (0 to 20 keV), B2 (20 to 40 keV), B3 (40 to 60 keV), B4 (60 to 80 keV), B5 (80 to 100 keV), B6 (100 to 120 keV), and B7 (120 to 140 keV). Depending on the energy value of the detected X-ray photon, the DAS adds the energy value to the counting result in the energy bin which is provided in association with the pertinent energy range.

Figure 4:
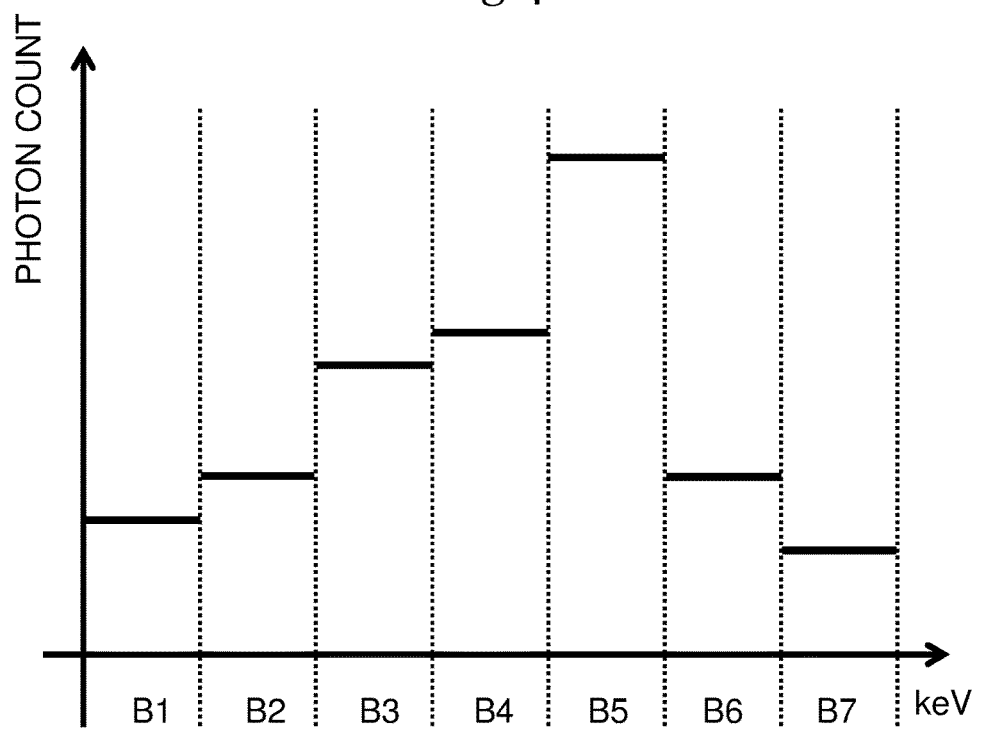
FIG. 4 illustrates a principle of X-ray photon counting of the photon counting CT device.

FIG. 4 shows an example of the calculation result above. As illustrated, the data collector 430 counts the number of X-ray photons, as to each energy range. As illustrated in the figure, the result being obtained shows a distribution of the energy values of the X-ray photons (the unit is keV). Therefore, the data collector 430 obtains an energy distribution (spectrum) of the X-rays detected by the X-ray detector 321. The data collector 430 outputs the obtained result, as count information.

The entire energy range, the first energy-range segments, i.e., the number of energy bins, and the energy range associated with each energy bin, may be configured according to instructions, and the like, from the user.

[Image Generator]

The image generator 450 reconstructs an X-ray CT image on the basis of the number of the X-ray photons (count information) being stored in each energy bin. The image is reconstructed, for example, by applying logarithmic transformation to the number of the X-ray photons. For the reconstruction, it is possible to use various known methods such as FeldKamp method and successive approximation.

In reconstructing the image, the image generator 450 may apply various correction processes to the count information. The correction processes here may include, circuit linearity correction, logarithmic transformation process, offset process, sensitivity correction, and beam hardening correction, and the like.

It should be noted that it is not necessary to use projection data stored in all the energy bins for generating the image. Only the projection data stored in the energy bin associated with a predetermined energy range may be used.

[Exposure Dose Estimator]

The exposure dose estimator 440 obtains an estimated exposure dose to the subject 101, in accordance with the imaging condition set by the user. In the present embodiment, X-rays in each energy range (energy band) according to predetermined second energy-range segments are applied with a predetermined irradiation intensity (unit irradiation intensity), and an exposure dose (exposure per band) obtained by this irradiation is used to estimate the exposure dose (estimated exposure dose) to the subject 101, the exposure dose being caused by the X-rays which are applied in accordance with the imaging condition.

In order to achieve the estimation above, the exposure dose estimator 440 is provided with a spectrum (energy distribution) acquisition part 441, and an estimated exposure dose calculator 442. The exposure per band DB 470 generated in advance may be used for calculating the estimated exposure dose.

The exposure dose estimator 440 of the present embodiment presents to the user, the calculated estimated exposure dose. By way of example, the estimated exposure dose may be presented on a monitor.

[Exposure Per Band DB]

The exposure per band DB 470 holds the exposure dose per unit irradiation intensity, in every energy range according to the predetermined second energy-range segments, as the exposure per band data.

The second energy-range segments are obtained by partitioning an assumed entire energy range of the X-ray photons, by a predetermined energy width $\Delta E$. The energy width $\Delta E$ may be 1 keV, for instance. By way of example, when the assumed entire energy range of the X-ray photons is set to be 0 to 140 keV, the exposure per band DB 470 partitions this entire energy range by $\Delta E$ (1 keV), into 140 energy ranges (energy bands), and stores the exposure dose per unit irradiation intensity in every energy range.

Figure 5:
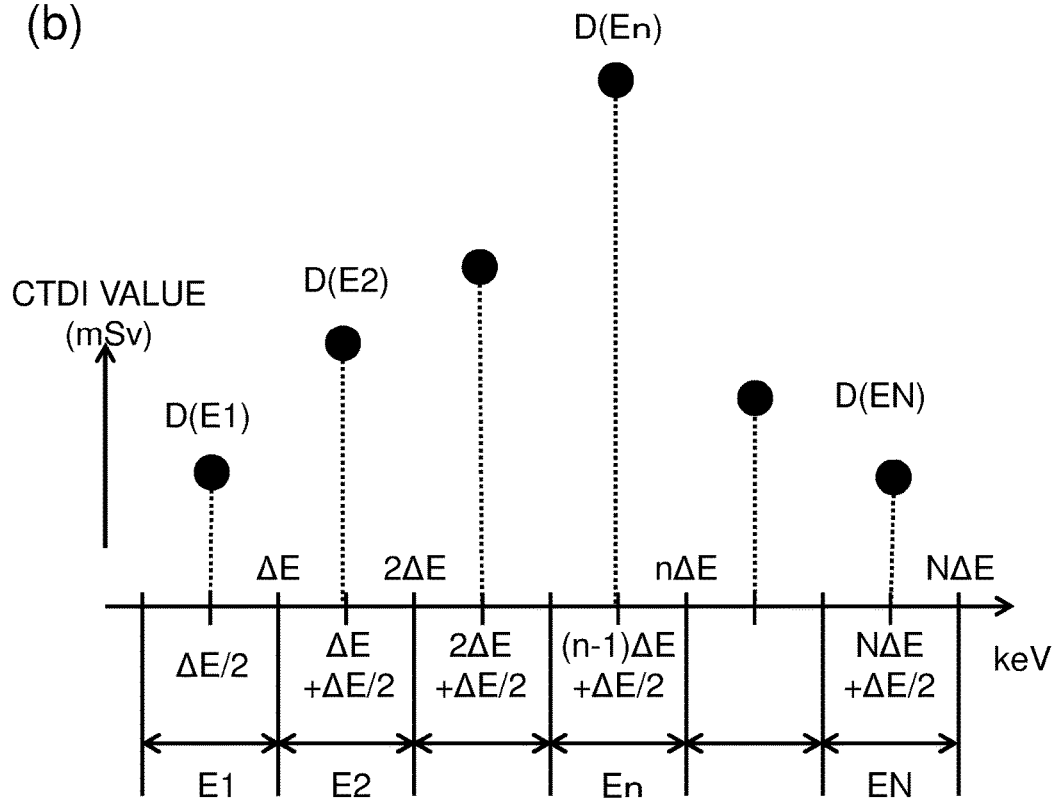
FIG. 5(a) illustrates an exposure per band database according to an embodiment of the present invention.
FIG. 5(b) illustrates data that is stored in the exposure per band database.

FIG. 5(*a*) illustrates an example of data held by the exposure per band DB 470. As illustrated, the exposure per band DB 470 stores the exposure per band, D(E1), D(E2), ... D(En), and ... D(EN), respectively in the energy ranges, E1, E2, ... En, and ... EN. It should be noted that N may be an integer at least one, and it may be 140, for instance. In addition, n may be an integer between or equal to one and N.

The exposure per band may be obtained by emitting X-rays with already-known energy from the X-ray tube 311 and actually measuring the X-rays. As shown in FIG. 6(*a*), for example, the actual measurement is performed by the X-ray measuring equipment 601, which is inserted into more than one position within a phantom 610. The phantom 610 is disposed at a location where the subject 101 is supposed to be placed. In this example here, a CTDI (Computed Tomography Dose Index) value (the unit is mSv) is employed as the exposure per band.

The CTDI value obtained by the actual measurement is a discrete value at an energy point (E) of the applied X-rays. In the exposure per band DB 470 of the present embodiment, this discrete value is assumed as the exposure per band in each energy range. In the present embodiment, the CTDI value D(E) actually measured by using the applied X-rays at the energy point E is assumed as the exposure per band, in the energy range with a width of $\pm\Delta E/2$ placing the energy point E at the center.

If the energy band width is represented by $\Delta E$, in the present embodiment, the CTDI values according to the X-rays respectively in the energy ranges E1 (0 to $\Delta E$ keV), E2 ($\Delta E$ to $2\Delta E$ keV), En (($n-1)\Delta E$ to $n\Delta E$ keV), ... E140 ($139\Delta E$ to $140\Delta E$ keV) are stored in the exposure per band DB 470. In this situation, as shown in FIG. 5(*b*), the CTDI values in the respective energy ranges are represented by the CTDI values $\Delta E/2$, $\Delta E+\Delta E/2$, ... $(n-1)\Delta E+\Delta E/2$, and $139\Delta E+\Delta E/2$, according to the X-rays at the respective energy points.

In creating the exposure per band DB 470, monochrome radiation or a radioactive source that emits radiation with predetermined energy, may be used.

When the radioactive source is used, only X-rays or γ-rays having the energy peculiar to a radioactive material being employed, can be obtained. By way of example, when amerisium-241 ($^{241}$Am) is employed, γ-rays of 59.5 keV are generated. When iodine-125 ($^{125}$I) is employed, γ-rays of 35 keV and 27 keV are generated. Similarly, other radioactive sources may generate only γ-rays having certain energy.

Therefore, it is difficult to obtain the exposure per band as to all the necessary energy, by using the radioactive source only. Given these circumstances, the radioactive sources may be used to measure specific measurable energy, and the other energy therebetween may be calculated by interpolation using the measured data. In other words, plural radioactive sources respectively having different energy values are used, and the exposure doses calculated by using the plural different-energy radioactive sources are interpolated, so as to obtain the exposure per band in every energy range, thereby generating the exposure per band DB 470.

The exposure per band DB 470 is not necessarily generated by actual measurement. By way of example, a Monte Carlo simulation may be used to calculate the exposure per band in every energy range. The Monte Carlo simulation treats physical phenomena concerning radiation behavior, as a probability matter, and uses random numbers to trace a physical process of the radiation (particles). In this case, it is desirable to compare a simulated result with an actual measured value, as to an energy value that is measurable by the radioactive source, and apply corrections to the comparison result.

This exposure per band DB 470 is created in advance, at the timing prior to imaging, such as when the device is manufactured and when the device is installed. In this case, the energy range width $\Delta E$ may be made narrower, thereby obtaining the estimated exposure dose more precisely.

The exposure dose in every energy range may not be derived from the X-ray having predetermined unit irradiation intensity. It may be derived from X-rays having intensity different respectively. In this case, the exposure per band DB 470 also stores the X-ray intensity which is used in calculating the exposure dose. Then, the estimated exposure dose is calculated, considering the X-ray intensity that was used when data was acquired.

[Spectrum Acquisition Part]

The spectrum acquisition part 441 obtains an energy distribution (spectrum) of the X-rays emitted from the X-ray tube 311 in accordance with the imaging condition set by the imaging condition setter 410, on the basis of the count information as to each of the energy-range segments, the count information being collected by the data collector 430. As shown in FIG. 6(b), the spectrum is obtained without placing the subject 101.

At the time of actual imaging, an X-ray filter 312, a bowtie filter 313, or the like, may be employed. The spectrum acquisition part 441 acquires a spectrum, in the state that such filters used in the actual imaging are installed.

In other words, the spectrum acquisition part 441 of the present embodiment instructs the measurement controller 420 so that X-rays are emitted according to the imaging condition, without placing the subject 101, and the spectrum is acquired. In the present embodiment, since the device is the PCCT device 100, the photon counts (energy value; X-ray dose) in every energy range according to the first energy-range segments are acquired, and generates a spectrum therefrom. Therefore, the spectrum acquired by the spectrum acquisition part 441 may be a discrete spectrum representing X-ray intensity incident on the X-ray detector 321 in every energy range according to the first energy-range segments.

In the following, a description will be made, assuming that in the present embodiment, each energy range width $\Delta B$ according to the first energy-range segments in the PCCT device 100 is equal to each energy range width $\Delta E$ according to the second energy-range segments, corresponding to the interval used in the exposure per band DB 470 described below, and those energy ranges are identical.

[Estimated Exposure Dose Calculator]

The estimated exposure dose calculator 442 calculates an estimated exposure dose, by using exposure per band data being exposure data per unit irradiation intensity of X-rays, in each energy range (energy band) according to the predetermined second energy-range segments, and the spectrum acquired by the spectrum acquisition part 441. In other words, by using the value in the exposure per band DB 470 and the spectrum acquired by the spectrum acquisition part 441, the exposure dose (estimated exposure dose) to the subject 101 is calculated, in the case where imaging is performed in accordance with the imaging condition being provided.

As for the energy value E, when the exposure per band is represented by D(E) and the spectrum is represented by S(E), the estimated exposure dose EsD(E) for this energy value E is expressed by the formula 1:

$$EsD(E) = D(E) \times S(E) \quad (1)$$

The estimated exposure dose $EsD_{all}$ calculated by the estimated exposure dose calculator 442 is obtained by accumulating EsD(E), as to all the energy ranges. Accordingly, it can be expressed by the following formula 2:

[Formula 2]

$$EsD_{all} = \int_E S(E) \times D(E) \quad (2)$$

It should be noted that D(0) indicates exposure caused by the photons having energy 0, and thus it is expressed as 0 (D(0)=0).

As described above, values of the exposure per band D held by the exposure per band DB 470 and the spectrum S acquired by the spectrum acquisition part 441 may be discrete values having an interval $\Delta E$. Therefore, the estimated exposure dose calculator 442 calculates estimated exposure dose $EsD_{all}$, actually according to the formula 3:

[Formula 3]

$$EsD_{all} = \sum_{i=1}^{\infty} S(i\Delta E) \times D(i\Delta E) \quad (3)$$

where $S(i\Delta E)$ is a spectrum of the energy bands from $(i-1)\cdot\Delta E$ to $i\cdot\Delta E$, and $D(i\Delta E)$ is the exposure per band in the energy bands from $(i-1)\cdot\Delta E$ to $i\cdot\Delta E$.

In the aforementioned formula 3, the range of the sum total is assumed as from 1 to infinity, for reasons of convenience. Actually, however, the upper limit of photon energy being generated is determined by a voltage value set by the X-ray source, and thus accumulation may be performed within the range up to the determined limit. By way of example, assuming the energy range is from 0 to 140 keV and $\Delta E$ is 1 keV, the formula 3 above is expressed by the following formula 4:

[Formula 4]

$$EsD_{all} = \sum_{i=1}^{140} S(i\Delta E) \times D(i\Delta E) \quad (4)$$

As described above, the estimated exposure dose calculator 442 of the present embodiment multiplies the exposure per band in each energy range according to the first energy-range segments, by the X-ray intensity in the energy-range segment, thereby calculating the estimated exposure dose in the energy-range segment. Then, the estimated exposure doses in the respective energy-range segments are added up, thereby obtaining the estimated exposure dose in the entire energy range.

[Flow of Imaging Process]

Figure 7:
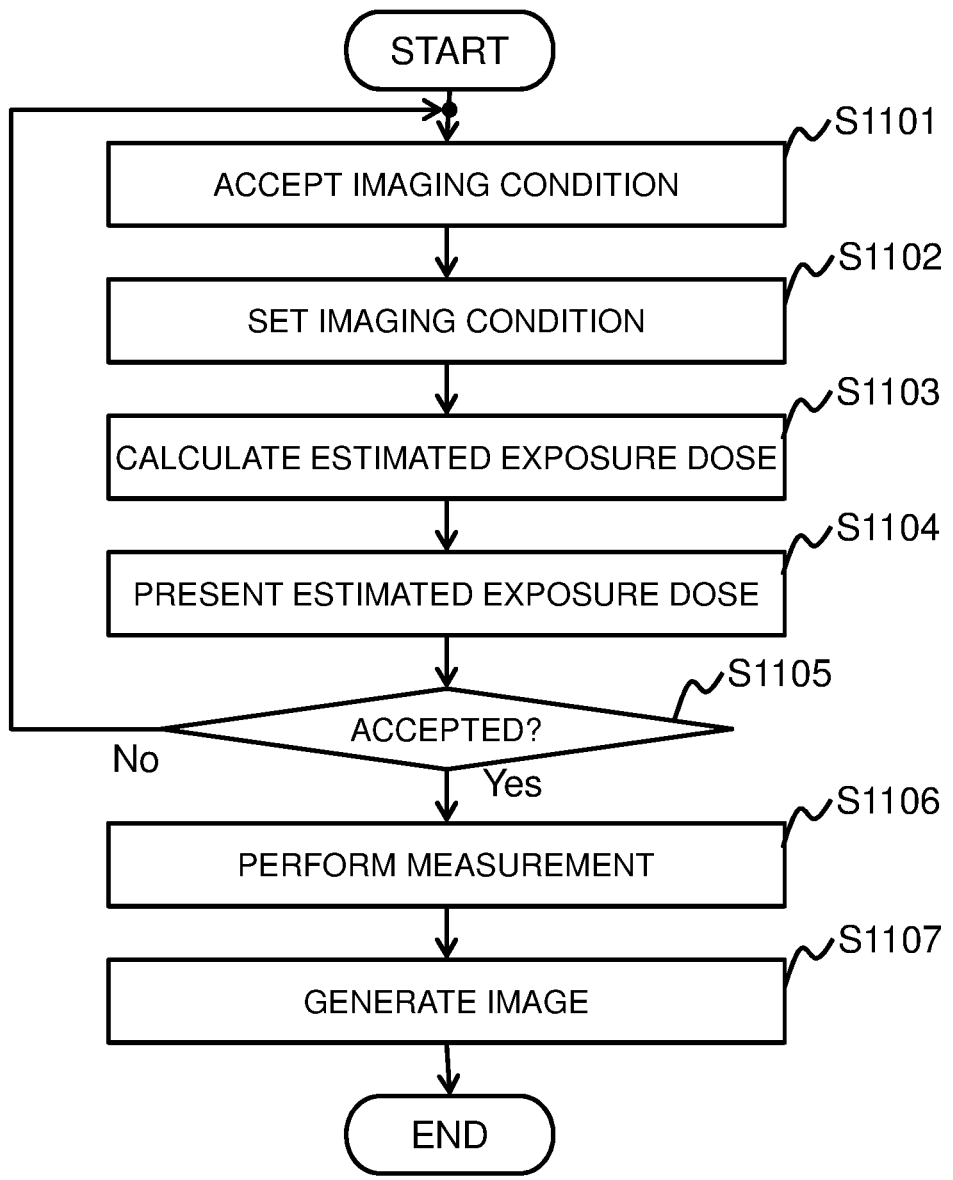
FIG. 7 is a flowchart of an imaging process according to an embodiment of the present invention.

Next, a flow of the imaging process by the operation part 400 of the present embodiment will be described. FIG. 7 is a flowchart of the imaging process according to the present embodiment. It is assumed that the exposure per band DB 470 is generated in advance.

Firstly, the imaging condition setter 410 accepts an imaging condition from the user via the UI part 200 (step S1101), and sets the condition (step S1102). The input-acceptable imaging conditions, may include tube voltage, tube current, a thickness and a form of the X-ray filter 312, a form of the bowtie filter 313, and the like.

Next, the exposure dose estimator 440 calculates the estimated exposure dose in accordance with the imaging condition being accepted (step S1103). Then, the exposure dose estimator 440 presents a result of the calculation to the user (step S1104), and accepts entry of yes or no (step S1105). It is further possible to configure such that the exposure dose estimator 440 presents as the calculation result, not only the estimated exposure dose, but also the spectrum.

In the step S1105, when an entry of "yes" from the user is accepted, the measurement controller 420 executes measurement according to the imaging condition set in the step S1102 (step S1106), and the data collector 430 collects data.

Thereafter, the image generator 450 generates an image from the data collected by the data collector 430 (step S1107), and completes the processing.

On the other hand, in the step S1105, when an entry of "no" from the user is accepted, the process returns to the step S1101, and the imaging condition setter 410 accepts a new imaging condition.

When the entry of "no" is accepted, it is alternatively possible to configure such that the imaging condition setter 410 modifies the imaging condition automatically, instead of accepting an entry of the new imaging condition from the user. In this case, the process returns to the step S1102, then the modified imaging condition is set, and the process is repeated.

The entry of "no" may be placed, typically in the case where the estimated exposure dose is large. Therefore, it is possible to configure such that the tube voltage is reduced automatically, for instance. Alternatively, only an instruction to increase or decrease the exposure dose is accepted from the user, and in response to the instruction, the tube voltage may be changed only by a predetermined amount of voltage.

In the step S1105, the estimated exposure dose is presented to the user, and an entry of yes or no is accepted, but this is not the only configuration. By way of example, in the step S1105, the imaging condition setter 410 may make determination automatically and modify the imaging condition as necessary, in response to the estimated exposure dose calculated in the step S1103, without presenting to the user, the estimated exposure dose.

In this case, a threshold for determining yes or no may be held in advance. In addition, a parameter to be changed and its amount of change (e.g., an amount of change $\Delta V$ of the tube voltage) are also held, for the case where it is determined as "no".

In other words, if the estimated exposure dose calculated in the step S1103 is equal to or less than the threshold, the imaging condition setter 410 permits transition to the step S1106 to perform measurement. On the other hand, when it is larger than the threshold, the imaging condition setter 410 reduces the tube voltage from the current value only by $\Delta V$, and repeats the process from the step S1102.

[Flow of Estimated Exposure Dose Calculation Process]

Figure 8:
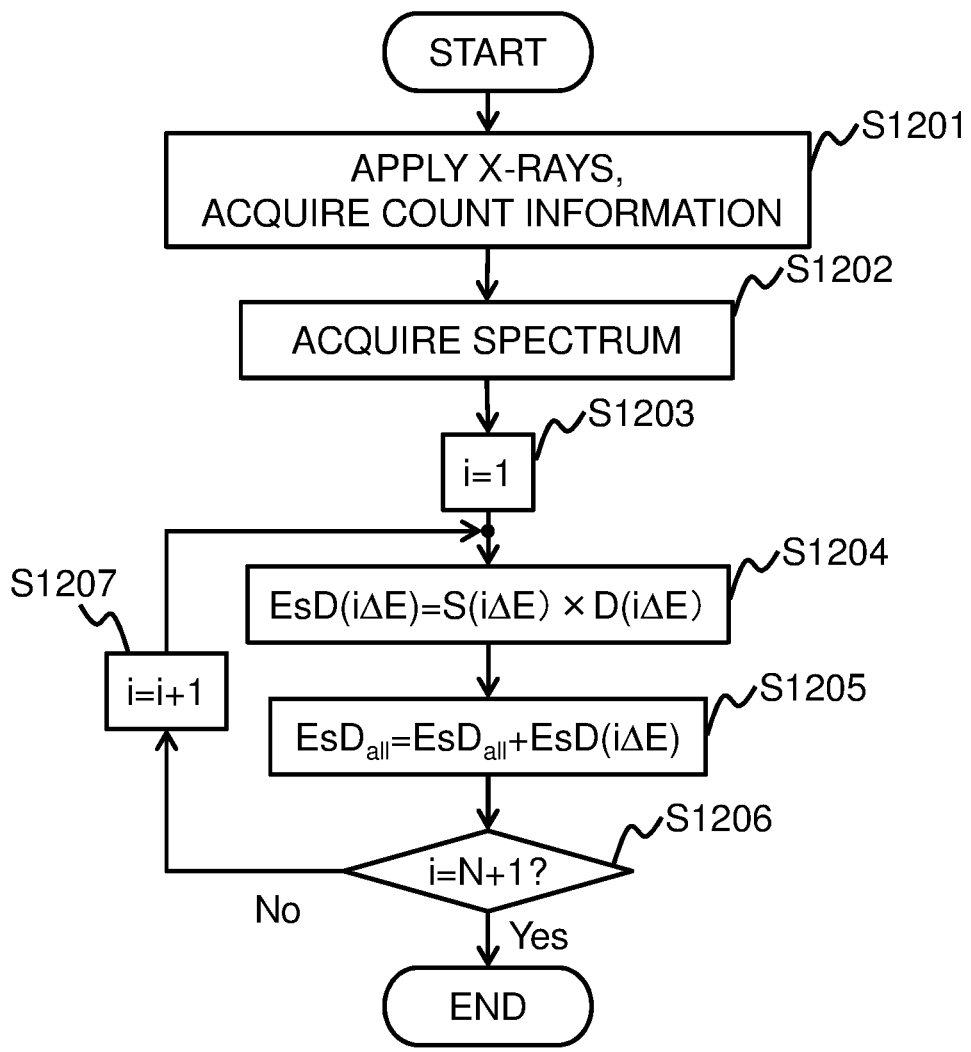
FIG. 8 is a flowchart of an estimated exposure dose calculation process according to an embodiment of the present invention.

Next, with reference to FIG. 8, a flow of the estimated exposure dose calculation process of the step S1103 will be described. In this example, the width of the energy range is represented by $\Delta E$, and the number of the energy ranges (the number of segments) is represented by N.

The exposure dose estimator 440 instructs the measurement controller 420 and the data collector 430 to count the X-rays applied and detected without placing the subject 101, in accordance with the imaging condition at the point of time, so as to obtain count information (step S1201). On the basis of the count information, the spectrum acquisition part 441 acquires a spectrum (energy values (X-ray intensity) in the respective energy ranges) (step S1202).

Next, the estimated exposure dose calculator 442 calculates the estimated exposure doses in all the energy ranges. Firstly, the counter i is initialized (i=1) (step S1203).

Then, the estimated exposure dose calculator 442 calculates the estimated exposure dose EsD (i$\Delta E$) of the energy range (band) in the i-th energy range, that is, in the ranges from (i−1)·$\Delta E$ to i·$\Delta E$ (step S1204). As described above, the calculation is made by multiplying the exposure per band D (i$\Delta E$) in the energy range (band) held by the exposure per band DB 470, by the spectrum S (i$\Delta E$).

Then, the estimated exposure dose calculator 442 adds the estimated exposure dose EsD (i$\Delta E$) in the i-th energy range (band) being calculated, to the estimated exposure dose $EsD_{all}$ in all the energy ranges (step S1205).

The estimated exposure dose calculator 442 repeats the processing above until the counter i becomes larger than the number of all the segments N (steps S1206 and S1207). Then, the estimated exposure dose $EsD_{all}$ at the point of time when the counter i becomes N+1 is assumed as the estimated exposure dose, and the processing is completed.

In the estimated exposure dose calculation process described above, the estimated exposure dose EsD (i$\Delta E$) calculated as to each energy range is added to $EsD_{all}$ calculated so far, thereby obtaining the estimated exposure dose in all the segments, but the process is not limited to this example. It is alternatively possible to configure such that after calculating the estimated exposure doses EsD(i$\Delta E$) respectively in the energy ranges, all the estimated exposure doses are added up.

[Correction Part]

As shown in FIG. 3, the exposure dose estimator 440 may also be provided with the correction part 443. This correction part 443 corrects influence of scattered radiation on the estimated exposure dose that is calculated by the estimated exposure dose calculator 442. In the present embodiment, the correction part 443 performs correction by subtracting a scattered radiation amount from the energy value in every energy range according to the first energy-range segments, the energy value being acquired by the spectrum acquisition part 441.

Firstly, the necessity of the scattered radiation correction will be described briefly. Even in the case where the subject 101 is not placed, scattered radiation which is caused by the collimator 323 in front of the detector element 322 of the X-ray detector 321, and rearward scattered radiation from a substrate and the like, not illustrated, at the back of the X-ray detector 321, may be incident on the X-ray detector 321. Under ordinary circumstances, such scattered radiation spreads entirely, causing deterioration of spatial resolution more or less, and this may only pose an impact on an image quality. However, for the case of the exposure estimation, it looks as if such scattered radiation increased the exposure dose. Thus, this may be a factor of misleading that there has been exposure to radiation equal to or more than emission. Accordingly, it is necessary to calculate an amount of the scattered radiation which is incident on the X-ray detector 321, from the collimator 323 and the substrate at the back of the X-ray detector 321, and to eliminate the scattered radiation.

The scattered radiation amount in every energy-range segment is calculated, which is incident on the detector elements 322, according to the Monte Carlo simulation that includes the collimator 323 and the substrate at the back of the detector element 322, for instance, thereby estimating the scattered radiation amount.

Therefore, for correcting the influence of the scattered radiation, when the spectrum acquisition part 441 acquires the energy value (measured X-ray dose) in every energy range according to the first energy-range segments, the correction part 443 calculates according to the Monte Carlo simulation, the scattered radiation amount with respect to each energy range, which is incident on the detector elements 322. Then, the correction part 443 subtracts the scattered radiation amount from the measured X-ray amount with respect to each energy range, and obtains a dose after the correction.

Then, the estimated exposure dose calculator 442 estimates the exposure dose, by using the dose after the correction. In other words, the dose after the correction is substituted into S(iΔE) in the formula 3 above, thereby calculating the estimated exposure dose $EsD_{all}$. By providing the correction part 443 as described above, the estimated exposure dose can be calculated more precisely.

As discussed so far, the PCCT device 100 of the present embodiment is provided with the X-ray emitter 310 for emitting X-rays, the X-ray detector 321 using a photon counting system for detecting the X-rays, the data collector 430 for counting the X-rays photons derived from the X-rays which are detected by the X-ray detector 321, as to each energy range according to the predetermined first energy-range segments and for obtaining count information in every energy range, and the exposure dose estimator 440 for obtaining an estimated exposure dose to the subject 101 according to the imaging condition set by the user, wherein the exposure dose estimator 440 is provided with the spectrum acquisition part 441 for obtaining a spectrum being an energy distribution of the X-rays emitted from the X-ray emitter 310 in accordance with the imaging condition, from the count information in every energy range according to the first energy-range segments, and the estimated exposure dose calculator 442 for calculating the estimated exposure dose, by using the spectrum as described above, and the exposure per band data which is exposure dose data per unit irradiation intensity of the X-rays, as to each energy range according to the predetermined second energy-range segments.

The exposure per band database 470 for holding the exposure per band data in every energy range according to the second energy-range segments may also be provided. The exposure per band database 470 may be created by interpolating the exposure doses which are calculated by using plural different-energy radioactive sources. The exposure dose estimator 440 may further be provided with the correction part 443 for correcting influence of the scattered radiation on the estimated exposure dose thus calculated. A monitor may also be provided for displaying thus calculated estimated exposure dose. The monitor may further display the spectrum of the X-rays.

According to the present embodiment as described above, the PCCT device 100 allows estimation of an exposure dose precisely, in a simple configuration, irrespective of the spectrum shape of the applied X-rays. Therefore, even when the applied spectrum shape varies with the use of a filter, or the like, it is possible to estimate the exposure dose precisely in accordance with the imaging condition, thereby improving precision in controlling the exposure dose to the subject 101. Accordingly, this enables efficient examination to be executed.

Modification Example 1

In the aforementioned embodiment, descriptions have been made, assuming that each energy range (the energy ranges according to the first energy-range segments) of the energy bins set in the PCCT device 100, coincides with each energy range (the energy ranges according to the second energy-range segments) of the exposure per band DB 470.

In other words, in the aforementioned embodiment, the data collector 430 sets the energy bin per unit band ΔE, and counts the X-ray photons, and the spectrum acquisition part 441 obtains X-ray intensity as to each energy range that coincides with the energy range of the exposure per band DB 470, so as to obtain a spectrum.

Actually, however, the band width of the energy bin (energy range width) ΔB may be different from each energy range width ΔE of the exposure per band DB 470. A method of handling this situation will be described in the present modification example.

Byway of example, as described above, the energy range width of the exposure per band DB 470 is set to 1 keV. However, setting the band width of the energy bin of the PCCT device 100 to 1 keV may enormously increase data volumes. Assuming that the maximum energy of the X-ray tube 311 as 120 keV, the number of the energy bins are required to be 120, and the spectrum acquisition part 441 has to categorize X-ray photons into 120 energy bands. Similar processing may be required in the subsequent measurement process.

Figure 9:
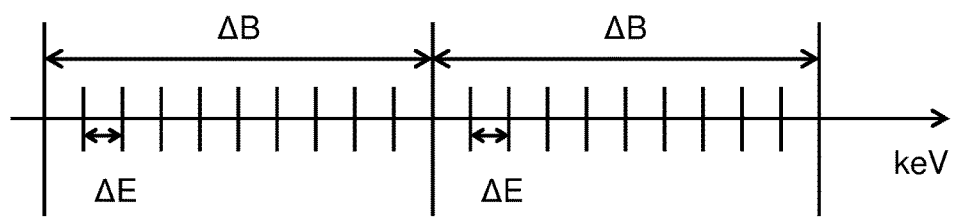
FIG. 9 illustrates each energy range width of the first modification example according to an embodiment of the present invention.

In other words, in the PCCT device 100, a data amount to be transferred is increased along with arise of the number of the energy bins, and a throughput may be increased accordingly. Therefore, in many cases generally, as shown in FIG. 9, the energy band width ΔB is configured to be larger than the energy range width ΔE of the exposure per band DB 470 (ΔB>ΔE), in order to put the transfer data amount and the throughput into a predetermined range. FIG. 9 shows an example that ΔB is ten times larger than ΔE.

As thus described, when the energy range width ΔE of the exposure per band DB 470 is different from the energy bin band (energy band width) ΔB of the PCCT device 100, in particular, when the energy bin band ΔB is larger than the energy range width ΔE, the estimated exposure dose calculator 442 combines both widths, so as to perform the multiplication.

In other words, when the values of ΔB and ΔE are different, the estimated exposure dose calculator 442 converts either one of the count information and the exposure per band data, into a value acquired according to the other energy-range segments, thereby calculating the estimated exposure dose.

As a method of the conversion, there are two methods; a method (first method) for converting the exposure per band of the exposure per band DB 470 into a value of each energy range of the energy bin, and a method (second method) for converting the X-ray intensity in each energy range of the energy bin acquired by the spectrum acquisition part 441, into a value in each energy range of the exposure per band DB 470.

In the first method, an average value of the exposure per band in every energy range according to the first energy-range segments of the exposure per band DB 470 is calculated, and set the result as the exposure per band in each energy range according to the first energy-range segments.

By way of example, assuming the energy range width ΔE of the exposure per band DB 470 as 1 keV, the exposure per band DB 470 holds the amounts of exposure per band D, respectively in the energy ranges 0 to 1 keV, 1 to 2 keV, 2 to 3 keV, . . . , 9 to 10 keV, 10 to 11 keV, and so on. Assuming the energy range width ΔB of the PCCT device 100 as 10 keV and the maximum tube voltage as 120 keV, the spectrum acquisition part 441 acquires the X-ray intensity respectively in the energy ranges, 0 to 10 keV, 10 to 20 keV, 20 to 30 keV, . . . , and 110 to 120 keV.

The estimated exposure dose calculator 442 extracts 10 amounts of exposure per band, respectively in 0 to 1 keV, 1 to 2 keV, 2 to 3 keV, . . . , 9 to 10 keV of the exposure per band DB 470, calculates an average of those values, and the average value is assumed as the exposure per band in the energy range 0 to 10 keV. Similar calculation is performed for the remaining energy ranges, and the exposure per band of each energy range according to the first energy-range segments is obtained.

In the second method, the estimated exposure dose calculator 442 obtains X-ray intensity in narrower energy ranges by interpolation, from the X-ray intensity in every energy range according to the first energy-range segments acquired by the spectrum acquisition part 441. Firstly, a mean energy value of each energy range according to the first energy-range segments is determined as a value of each energy range according to the second energy-range segments. Then, by the interpolation using thus determined value, a value in another energy range according to the second energy-range segments is calculated.

By way of example, assume that the energy range width $\Delta B$ according to the first energy-range segments is 10 keV, and the energy range width $\Delta E$ according to the second energy-range segments is 1 keV. On this occasion, the estimated exposure dose calculator 442 converts the X-ray intensity in every energy range width acquired by the spectrum acquisition part 441, into the X-ray intensity in $\frac{1}{10}$ of the energy range width.

In this case, for example, as for the spectrum in the range of 0 to 10 keV, the X-ray intensity in the energy range around 5 keV being the mean value, incremented by 1 keV, is set to be $\frac{1}{10}$ of the initial value. Subsequently, as for the range of 10 to 20 keV, the X-ray intensity in the energy range around 15 keV incremented by 1 keV, is set to be $\frac{1}{10}$ of the initial value, and as for the range of 20 to 30 keV, the X-ray intensity in the energy range around 25 keV incremented by 1 keV, is set to be $\frac{1}{10}$ of the initial value. On the basis of thus obtained X-ray intensity values respectively of 5 keV, 15 keV, 25 keV, and so on, the X-ray intensity values respectively in all the energy ranges, incremented by 1 keV, are obtained according to interpolation.

Since 0 keV indicates that there is no energy, the X-ray intensity of the X-ray photons in this case is assumed to be zero. When the tube voltage is maximum (e.g., assume it is 120 kV), X-rays exceeding this tube voltage are not generated. Therefore, the X-ray intensity of the X-ray photons at the maximum tube voltage is also assumed to be zero. According to the interpolation on the basis of those boundary values and the X-ray intensity of 5 keV, 15 keV, and so on, the X-ray intensity in every energy range is obtained. By way of example, this interpolation may be linear interpolation, spline interpolation, or the like.

According to the present modification example, even when the energy bin band $\Delta B$ is different from the energy width $\Delta E$ of the exposure per band DB 470, the exposure dose can be estimated precisely. In the PCCT device 100, even in the case where counting is not allowed to be performed according to the unit of energy range equivalent to the unit of exposure per band, it is possible to estimate the exposure dose precisely, irrespective of the spectrum shape.

In addition, since the energy bin width $\Delta B$ can be set freely, it is possible to reduce an amount of transfer data, in obtaining the spectrum, by setting the energy bin width wider.

As a further alternative modification example, instead of the conversion after acquiring the spectrum, it is further possible to configure such that the energy range is made to vary for each measurement at every measurement time, whereby a spectrum having the energy range coincident with the energy range of the exposure per band DB 470 is obtained.

By way of example, the number of the energy bins is assumed to be 12. By using those 12 energy bins, in the first measurement, measurement is performed in the energy range of 0 to 12 keV, and in each of the energy bins, X-ray photons are counted, respectively in the energy bands of 0 to 1 keV, 1 to 2 keV, ... and 11 to 12 keV. Subsequently in the second measurement, measurement is performed in the energy range of 12 to 24 keV, and in each of the energy bins, X-ray photons are counted, respectively in the energy bands of 12 to 13 keV, 13 to 14 keV, ... , and 23 to 24 keV. By repeating the measurement 10 times, measurement of the energy range of 0 to 120 keV is implemented.

The measurement controller 420 controls the measurement in the manner as described above, thereby achieving measurement of much narrower energy band width, using the same number of energy bins. Therefore, even in the case where the PCCT device includes a small number of energy bins, X-ray intensity can be obtained for every energy range, equivalent to those of the exposure per band DB 470, allowing the estimated exposure dose calculator 442 to calculate the estimated exposure dose with a high degree of precision.

Modification Example 2

In the aforementioned embodiment, the exposure dose is figured out, according to the estimated exposure dose only. However, this is not the only example. In another instance, it is also possible to configure such that an image acquired in accordance with the imaging condition is presented to the user as reference data, and prompting the user to make a judgment.

Figure 10:
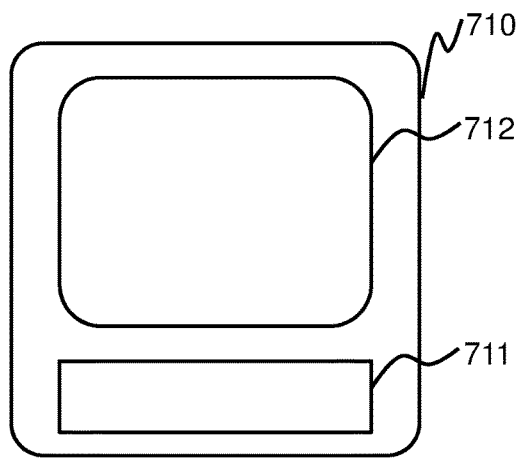
FIG. 10(a) illustrates an image database according to an embodiment of the present invention.
FIG. 10(b) illustrates an example of a display image according to an embodiment of the present invention.
FIG. 10(c) illustrates the estimated exposure dose database according to an embodiment of the present invention.

In this case, as shown in FIG. 10(*a*), the operation part 400 is further provided with an image database (image DB) 490 holding images that are acquired in association with the imaging conditions. The image DB 490 may be constructed in the HDD unit 403.

[Image Database]

The image DB 490 is created by storing image data acquired respectively in association with the imaging conditions used in acquiring the image, every time of image acquisition. In the present modification example, as illustrated in FIG. 10(*a*), the image DB 490 holds image data in association with the imaging condition that has something to do with an image quality, among the imaging conditions, thereby allowing the image quality to be specified.

As the image-quality identifiable image data, for example, image data acquired in accordance with the pertinent imaging condition in the past, may be held. The imaging condition having an effect on the image quality may include tube voltage, tube current, the form of the X-ray filter 312, and the form of the bowtie filter 313, for instance.

The image data held in the image DB 490 may also be associated with physical constitution data of the subject 101. The physical constitution data of the subject 101 may include, height, weight, abdominal circumference, and chest circumference, for instance. In addition, if another image obtained in accordance with the same condition has already been held, upon storing the image, it may be newly updated.

In the present modification example, in the step S1104, the exposure dose estimator 440 presents to the user, an image held in the image database according to the imaging condition being provided, together with the estimated exposure dose. The image data being presented corresponds to the data held in the image DB 490 in association with the imaging condition that is provided when the image is presented.

FIG. 10(b) illustrates a screen example 710 being displayed. As illustrated, the estimated exposure dose 711 and the image data 712 are presented to the user. As described above, it is also possible to display the spectrum as well.

In the present modification example, if both data items thus presented are satisfactory for the user, in the step S1105, the results are determined as acceptable and the user instructs to perform imaging in step S1105, and if not, it is notified that the results are not acceptable. In the latter case, the process returns to step S1101, so as to change the imaging condition.

In the present modification example, both the estimated exposure dose and a quality of the image are presented to the user simultaneously. Therefore, the user is allowed to grasp those data items at the same time. Accordingly, the user is also allowed to understand diagnostic ability of the image being obtained, and prevents ineffective exposure due to insufficient radiation dose.

Modification Example 3

The operation part 400 may further be provided with an estimated exposure dose database (estimated exposure dose DB) 480 that holds estimated exposure doses that are calculated respectively in association with imaging conditions. In this case, the exposure dose estimator 440 refers to the estimated exposure dose DB 480, prior to acquiring the X-ray spectrum, and obtains an estimated exposure dose being held therein as the estimated exposure dose to the subject, when the estimated exposure dose has already been held in association with the imaging condition being provided.

In other words, when the estimated exposure dose associated with the imaging condition set by the imaging condition setter 410 has already been held in the estimated exposure dose DB 480, the exposure dose estimator 440 does not calculate the estimated exposure dose, but acquires the data from the estimated exposure dose DB 480.

FIG. 10(c) illustrates an example of this estimated exposure dose DB 480. As illustrated, the estimated exposure dose DB 480 stores the estimated exposure doses respectively in association with the imaging conditions. This estimated exposure dose DB 480 is created by the exposure dose estimator 440, which calculates the estimated exposure dose and holds the calculated estimated exposure dose every time of calculation, in association with the imaging condition which is provided upon calculating the estimated exposure dose. The estimated exposure dose DB 480 may be constructed in the HDD unit 403.

In this case, when the imaging condition is inputted, the exposure dose estimator 440 determines whether the imaging condition is coincident with the imaging condition stored in the estimated exposure dose DB 480, prior to acquiring a spectrum. If it is stored, instead of calculating using the aforementioned method, the stored estimated exposure dose is extracted from the estimated exposure dose DB 480 and it is used in the processing.

Accordingly, it is not necessary to calculate the estimated exposure dose every time the imaging condition is provided, allowing reduction of the time relating to calculation of the estimated exposure dose.

In the aforementioned embodiment and in each of the modification examples, the operation part 400 has been described as provided in the PCCT device 100, but this configuration is not restricted to this example. In another instance, the operation part 400 may be constructed in an information processing unit, independent of the PCCT device 10, which can transmit data to and receive data from the PCCT device 100.

Similarly, the UI part 200 may also be configured as an independent part which can transmit information to or receive information from the PCCT device 100.

In addition, the UI part 200 and the operation part 400 may be implemented as a single information processing unit.

The PCCT device 100 of the present embodiment may perform FFS (Flying focal spot) imaging, in order to enhance in-plane spatial resolution. If the FFS imaging is performed, a method for moving a focal spot of the X-ray tube 311 may be determined according to resolution of the subject 101, and the method is provided as one of the imaging conditions.

DESCRIPTION OF SYMBOLS

100: PCCT device, 101: subject, 102: table, 200: UI part, 210: input unit, 220: output unit, 300: measurement part, 310: X-ray emitter, 311: X-ray tube, 312: X-ray filter, 313: bowtie filter, 320: X-ray detection part, 321: X-ray detector, 322: detector element, 323: collimator, 330: gantry, 331: opening, 332: rotating panel, 340: controller, 341: emission controller, 342: gantry controller, 343: table controller, 344: detection controller, 400: operation part, 401: CPU, 402: memory, 403: HDD unit, 410: imaging condition setter, 420: measurement controller, 430: data collector, 440: exposure dose estimator, 441: spectrum acquisition part, 442: estimated exposure dose calculator, 443: correction part, 450: image generator, 470: exposure per band DB, 480: estimated exposure dose DB, 490: image DB, 601: X-ray measuring equipment, 610: phantom, 710: screen example, 711: estimated exposure dose, 712: image data

What is claimed is:

1. A photon counting CT device comprising,
an X-ray emitter configured to emit X-rays,
an X-ray detector using a photon counting system configured to detect the X-rays,
a data collector configured to count X-ray photons derived from the X-rays detected by the X-ray detector, in every energy range according to predetermined first energy-range segments, and to obtain count information as to each of the energy ranges, and
an exposure dose estimator configured to obtain an estimated exposure dose to a subject, in accordance with an imaging condition set by a user, wherein,
the exposure dose estimator comprises,
a spectrum acquisition part configured to obtain a spectrum, being an energy distribution of the X-rays emitted from the X-ray emitter in accordance with the imaging condition, on the basis of the count information as to each of the energy ranges according to the first energy-range segments, and
an estimated exposure dose calculator configured to calculate the estimated exposure dose, by using the spectrum, and exposure per band data being exposure data per unit irradiation intensity of the X-rays, in every energy range according to a predetermined second energy-range segments.

2. The photon counting CT device according to claim 1, comprising,
an exposure per band database configured to hold the exposure per band data in every energy range according to the second energy-range segments.

3. The photon counting CT device according to claim 1, wherein, the exposure dose estimator further comprises a correction part configured to correct influence of scattered radiation on the estimated exposure dose being calculated.

4. The photon counting CT device according to claim 2, wherein,
the exposure per band database is created by interpolating exposure doses calculated by using plural radioactive sources respectively having different energy.

5. The photon counting CT device according to claim 1, further comprising,
an estimated exposure dose database configured to hold the estimated exposure dose being calculated, in association with the imaging condition, wherein,
the exposure dose estimator refers to the estimated exposure dose database, prior to acquiring the spectrum, and obtains the estimated exposure dose being held therein as the estimated exposure dose to the subject, when the estimated exposure dose has already been held in association with the imaging condition being provided.

6. The photon counting CT device according to claim 1, wherein,
the estimated exposure dose calculator converts either one of the count information and the exposure per band data, into a value acquired according to the energy-range segments of the other, thereby calculating the estimated exposure dose.

7. The photon counting CT device according to claim 1, further comprising,
a monitor configured to display the estimated exposure dose being calculated.

8. The photon counting CT device according to claim 7, wherein,
the monitor further displays the spectrum.

9. The photon counting CT device according to claim 7, further comprising an image database configured to hold images respectively in association with imaging conditions, wherein,
the monitor further displays the image held in the image database, in accordance with the imaging condition being provided.

10. An estimated exposure dose calculation method in a photon counting CT device, comprising,
detecting X-rays emitted in accordance with an imaging condition set by a user,
counting X-ray photons derived from the X-rays being detected in every energy range according to predetermined first energy-range segments, and obtaining count information as to each of the energy ranges,
obtaining a spectrum being an energy distribution of the X-rays, on the basis of the count information, and
calculating an estimated exposure dose in accordance with the imaging condition, by using the spectrum, and exposure per band data being exposure data per unit irradiation intensity of the X-rays, in every energy range according to predetermined second energy-range segments.

* * * * *